United States Patent [19]
Rath et al.

[11] 3,942,361
[45] Mar. 9, 1976

[54] ARRANGEMENT FOR TESTING THICK-WALLED SPECIMENS BY THE ULTRASONIC PULSE-ECHO METHOD

[75] Inventors: Walter Rath, Turnich; Rudolf Worschech, Hamburg, both of Germany

[73] Assignee: Krautkramer-Branson, Incorporated, Stratford, Conn.

[22] Filed: Nov. 21, 1973

[21] Appl. No.: 418,134

Related U.S. Application Data

[63] Continuation-in-part of Ser. No. 353,321, April 23, 1973, abandoned.

[52] U.S. Cl. .................................................. 73/67.7
[51] Int. Cl.² .......................................... G01N 29/04
[58] Field of Search........... 73/67.7, 67.8 R, 67.8 S, 73/67.9, 71.5 US; 330/1 R, 2

[56] References Cited
UNITED STATES PATENTS

| | | | |
|---|---|---|---|
| 3,332,278 | 7/1967 | Wood et al. .......................... | 73/67.7 |
| 3,683,680 | 8/1972 | Johnson et al. ...................... | 73/67.7 |
| 3,685,348 | 8/1972 | Bottcher et al. .................. | 73/67.8 R |
| 3,690,153 | 9/1972 | Matay .............................. | 73/67.8 R |
| 3,759,090 | 9/1973 | McFaul et al..................... | 73/67.9 X |

Primary Examiner—Richard C. Queisser
Assistant Examiner—Stephen A. Kreitman
Attorney, Agent, or Firm—Howson and Howson

[57] ABSTRACT

In an ultrasonic pulse-echo test arrangement which is particularly suited for testing heavy-walled workpieces, a plurality of transducer probes are used. Two or more transmitting transducer probes are arranged so that each probe transmits its sound beam to a respective test zone, the zones being staggered relative to each other across the thickness of the workpiece. A defect in a respective zone reflects energy to a predetermined location at the rear wall of the workpiece, such location being common to all defect responsive reflected signals. A receiving transducer probe is disposed for receiving all of the defect responsive signals reflected from the stated location. Electrical circuit means cause the defect responsive signals generated in the receiving circuit to be of the same amplitude irrespective of location in the workpiece if the defects are of equal magnitude and cause, furthermore, the transmitted and received energy to be compensated for individual variations in the coupling quality between the respective probe and workpiece surface.

10 Claims, 8 Drawing Figures

| FIG. 5A |
| FIG. 5B |

ARRANGEMENT FOR TESTING THICK-WALLED SPECIMENS BY THE ULTRASONIC PULSE-ECHO METHOD

CROSS REFERENCE TO PENDING APPLICATION

This application is a continuation-in-part application of copending patent application Ser. No. 353,321, filed Apr. 23, 1973, now abandoned.

FIELD OF THE INVENTION

This invention relates to an arrangement for testing thickwalled workpieces using the ultrasound method. More specifically, this invention concerns an ultrasonic pulse-echo test arrangement for detecting flaws which are disposed perpendicular to the surface of the workpiece using two or more probes located at one surface of the workpiece whereby sound waves reflected from the opposite surface of the workpiece are received by at least one probe and the workpiece is divided into scanning zones.

BAACKGROUND OF THE INVENTION

Workpieces having a heavy wall, for example, pressure vessels made from conventional steel and provided with internal corrosion protection in the form of an autenitic cladding, must be scanned for cracks and particularly for incipient flaws. The prior art discloses several ultrasonic test processes applicable to this problem, such as are described by A. de Sterke, "Some Aspects of Radiography and Ultrasonic Testing of Welds in Steel with Thicknesses from 100–300 mm", Brit. J. NDT, December 1967, pp. 94–107; B. J. Lack, "Ultrasonic Examination of Welds in Thick Plates", Brit. Weld, J., February 1962, pp. 54–60; and W. Mohr, German OS No. 2,030,582. In these prior art descriptions a first ultrasonic probe applied to the surface of the workpiece usually transmits sound into the workpiece. A portion of the sound, upon being intercepted by a crack, is reflected toward the rear wall of the workpiece, and from there the reflected energy is reflected back again to the surface of the workpiece on which a second probe (receiver) is disposed, but of course at a spatially separated location. The receiver probe, therefore, must be located at the point at which the reflected energy, denoting a crack, can be sensed at the workpiece surface.

The size of a flaw, as long as its size is smaller than the sound beam, can be determined from the amplitude of the received ultrasonic signal. This determination is impossible if the reflection and acoustic energy attenuation characteristics existing at the reflection surface change continually from location to location along such surface. Changes in reflection characteristics at the reflection surface may affect the ultrasonic echo signal amplitude to a greater extent than the size of a defect itself.

Scanning thick-walled vessels using the so-called tandem method, that is with two probes which are disposed one behind the other, or side by side (see de Sterke supra) and forming an angle with each other (see Lack supra) is known by those skilled in the art. One transducer probe is used as the transmitter and the other as the receiver of ultrasonic energy. The distance between the probes is determined by the depth of the test zone below the surface of the workpiece and the beam angle.

Another known method is to provide dual probe units in such a manner that the entire cross-section of the workpiece is divided into vertical layers of test zones. One pair of probes is associated with each respective zone. If these pairs of probes are connected electronically with an ultrasonic instrument, a very rapid scanning of the complete cross-section of the workpiece is achieved.

It is further known, that the individual probes can be equipped with so-called coupling control probes which transmit ultrasonic energy into the workpiece in a direction perpendicular to the entrant surface of the workpiece and respond to the so-called rear wall echo responsive signals. The amplitude of the rear wall echo responsive signal serves as a measurement of the quality of the coupling achieved between the transducer probe and the workpiece entrant surface and can be used for controlling the receiver gain.

In summary, the known arrangements for scanning thick-walled specimens entail a relatively high degree of cost. The probes must be either mechanically adjusted to scan different zones, which is very time-consuming, or a large quantity of probes must be used and connected in respective pairs to the ultrasonic instrument. The greater the quantity of probes the more costly the entire test installation. It clearly must be kept in mind that different sound reflection and attenuation properties inherent in the workpiece not only need to be recognized but must be compensated for by the test apparatus.

A principal object of this invention is to reduce the quantity of probes used, provide a simplified determination of the reflection and attenuation properties, and to make use of these properties for adjusting the scanning sensitivity.

BRIEF SUMMARY OF THE INVENTION

In the preferred embodiment the centers of the test zones of a workpiece, at any instant of observation, are disposed staggered with respect to each other, and located along a common line which intersects the axes of the sound beams originating from an array of transmitting probes. This common line is such that upon the generation of a reflected sound beam, as from a crack in a respective zone, the line is common to the reflected sound beam axes over the remaining portion of the total path traversed by the sound. The receiving probe is located so that its beam axis intersects the opposite wall of the workpiece at the same location as the common line. Hence, the centers of all the test zones are disposed along a common line and the centers of all sound beams emanating from the various transmitting probes and received by the receiving transducer, after reflection at a crack in a respective zone, are subjected to identical reflection and attenuation losses by reason of the reflection of sound at the common location. Hence, cracks or flaws of equal size and located in the respective test zones will be indicated by echo signals of equal amplitude. The receiving transducer probe senses only those reflections which are received via reflection at the rear wall, regardless of their origin, and which have been subjected to identical attenuation and reflection losses.

A further object of this invention concerns an arrangement wherein at least one receiving probe is responsive to at least one transmitting probe and a compensating circuit is provided so that flaws of the same size, independent of the properties of the reflection location, are indicated with the same signal amplitude. It is further advantageous, in accordance with this invention, to use a gain control in the compensating circuit, which includes a nominal to actual value comparator for providing a variable gain signal applied to a control module so that the echo amplitude received via the rear wall reflection by a receiving probe is controlled to exhibit a constant amplitude. Another arrangement employing this method also provides that each individual probe tests its degree of acoustic coupling with the workpiece surface and the sensitivity of the scanning system is controlled in response to the coupling condition derived from such test.

DETAILED DESCRIPTION OF THE PREFERRED EMBODIMENT

Figure 1:
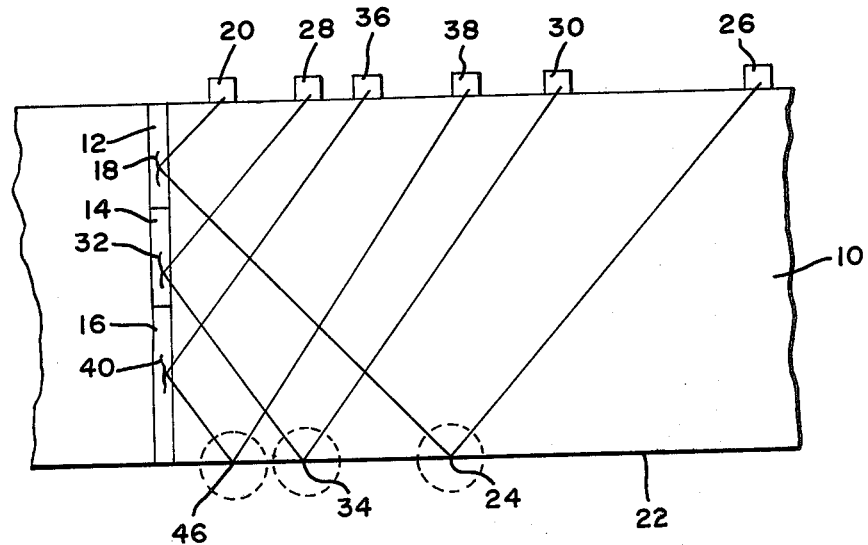
FIG. 1 is a sectional view of a test specimen showing the known arrangement of scanning zones and a quantity of probes arranged at the surface of the workpiece.

A section of a thick-walled specimen 10 is shown in FIG. 1. The cross-section of the wall is divided into three zones designated by numerals 12, 14 and 16. If a crack 18 perpendicular to the surface of the specimen is disposed in the first zone 12, then the sound transmitted by the probe 20 is reflected from this crack to the rear wall 22 and is reflected again from location 24 to the receiving probe 26. The same sequence occurs with the combination of probes 28 and 30 with respect to a crack 32 in zone 14 and location 34, and again with probes 36 and 38 with respect to a crack 40 in zone 16 and location 46. If there are no cracks or other discontinuities in scanning zones 12, 14 and 16, then there will be an absence of sound reflections to the corresponding receiving probes. An absence of echo signals appearing at the probes 26, 30 and 38 signifies that there are no cracks in the workpiece portion under test, no coupling between the probe and the workpiece surface, or too much signal attenuation in the workpiece.

In accordance with FIG. 1, two probes are positioned for testing a respective scanning zone, and reflections at the rear wall 22 are obtained from different locations designated by numerals 24, 34 and 46.

Figure 2:
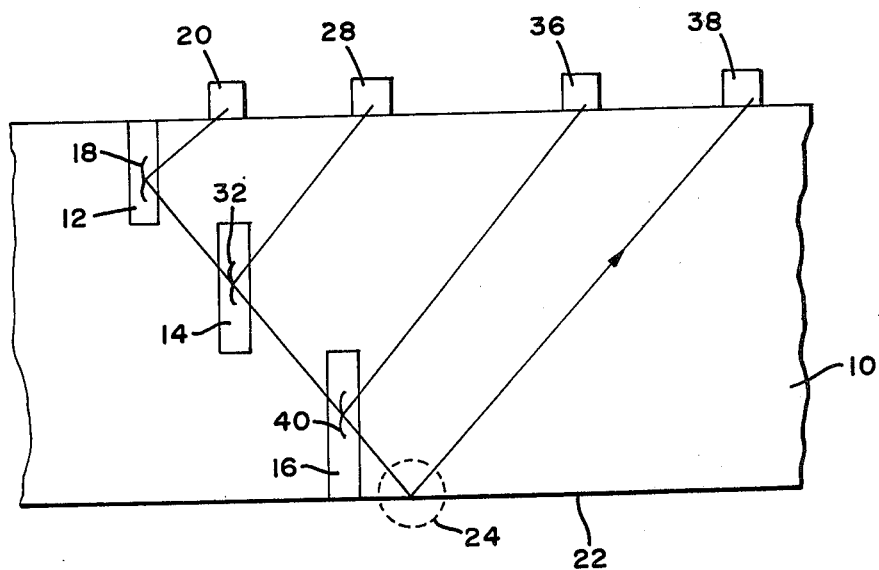
FIG. 2 is a view similar to FIG. 1, but with the scanning zones delineated according to the present invention.

In FIG. 2 the scanning zones are shifted to form a staggered grouping. The zones are no longer aligned vertically below each other, but exhibit a staircase type, staggered formation across the thickness of the workpiece. The arrangement, as before, is very much dependent upon the probe positions and the beam angle.

It is apparent that the essential advantage of the probe arrangement according to the invention resides in the feature that the quantity of probes has been reduced from six probes to four probes in the case of three zones, and from $2n$ to $n + 1$ in the general case of $n$ zones. It can be seen further that in FIG. 2 only a single reflection location 24 is used at the rear wall 22 for all three scanning zones and that a flaw in any of the zones 12, 14 or 16 will cause a defect responsive signal to appear at the receiving probe 38.

Figure 3:
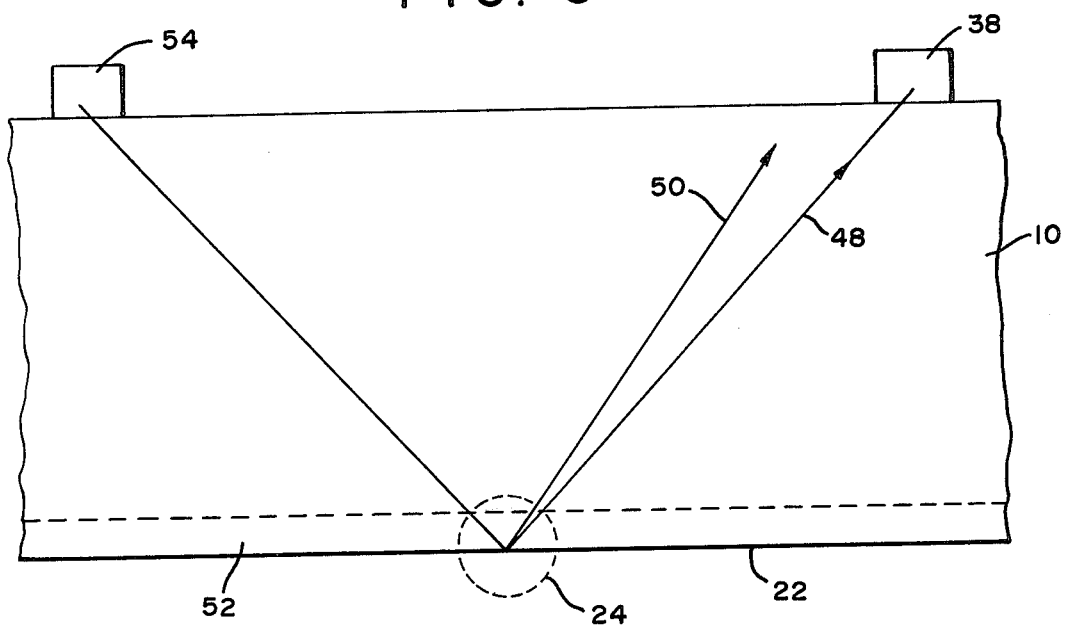
FIG. 3 is a similar view of a test specimen illustrating the condition when the reflection location at the rear surface of the specimen exhibits different reflection characteristics.

When the rear wall 22 is uneven, as indicated in FIG. 3, then the acoustic energy does not travel mainly along the path shown by line 48 to reach the probe 38, but a deviation, path 50, results. Only the smaller energy originating from the periphery of the sound beam will be received by the receiving probe 38.

If the rear wall is provided, furthermore, with austenitic cladding 52 as is commonly used in nuclear reactor construction, then the acoustic energy arriving at the receiving probe is attenuated to a considerable degree. Cladding of this type is shown in FIG. 3. The thicker the austenitic layer, the greater the degree of sound attenuation. Hence, as the probes are moved along the surface of specimen 10 the sound energy transmitted from probe 54, for example, subsequent to its reflection at the rear wall 22 of the workpiece 10, may exhibit relatively large variations. During the welding process unavoidable variations in the thickness of the austenitic cladding 52 occur and the receiving probe 38, therefore, does not receive a constant amount of reflected energy as is required for determining the size of a flaw by means of measuring the amplitude of the reflected signal.

Figure 4:
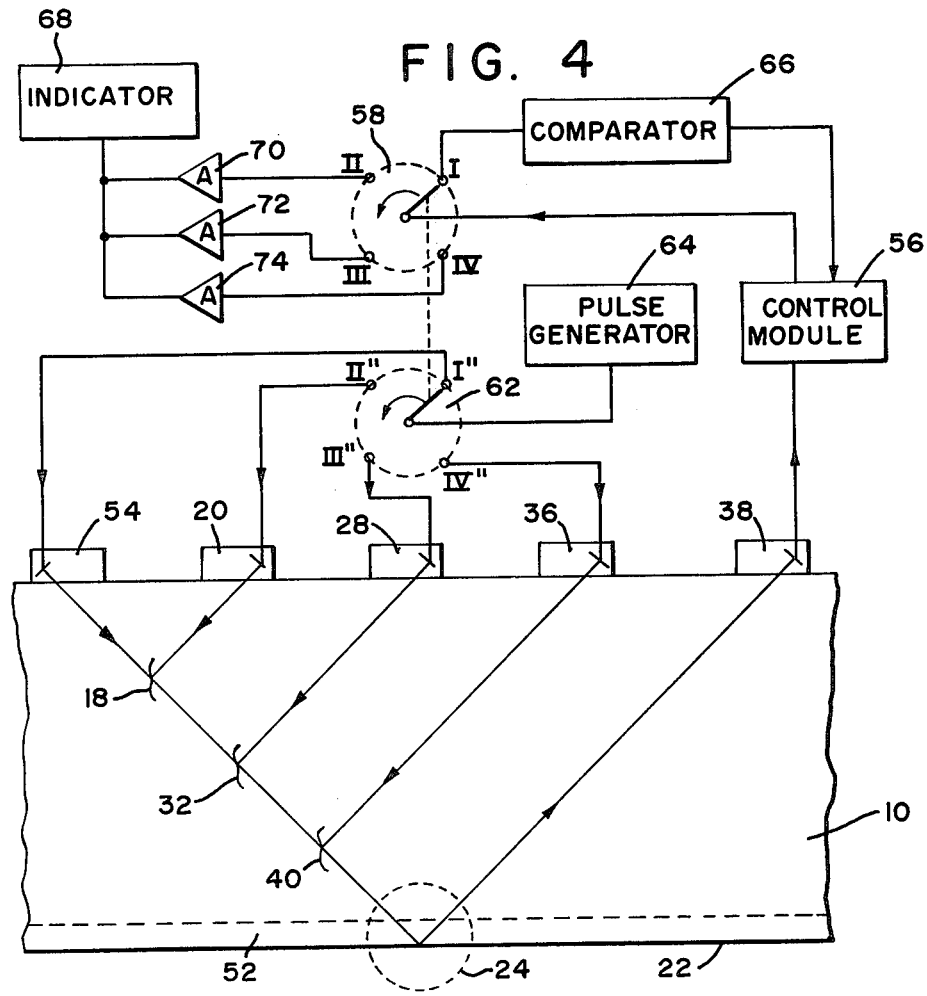
FIG. 4 is a schematic electrical block diagram showing a quantity of probes disposed for testing a specimen and including means for compensating for the sound reflection and attenuation characteristics at the rear wall of the specimen.

FIG. 4 shows schematically the manner by which the use of a nominal to actual value comparator 66 the gain of a control module 56 is controlled to cause the received signals from probe 38 to exhibit constant signal amplitude. Switches 58 and 62 while shown as mechanical embodiments, are preferably of the electronic type.

When the switches 58 and 62 are set to the position I and I'' respectively, the pulse generator 64 is connected via switch 62, position I''', to the transmitting probe 54. The receiving probe 38 is positioned for receiving the acoustic energy after the transmitted signal has been reflected at the location 24 of the rear wall 22. The receiving probe 38 passes the received signal via the control module 56 and switch 58, position I, to the nominal to actual value comparator 66 which performs the nominal to actual signal comparison and provides a signal for controlling the control module 56 responsive to the difference between the received signal and the nominal value signal. This step sets the signal level of the control module 56 and the control module 56 may now be considered to be "normalized". The circuit of the control module 56 has a relatively long time constant and a set (normalized) condition will remain substantially constant during the time in which the switches 58 and 62 complete one cycle of rotation. Only after one cycle of rotation of the switches will the signal supplied to the control module 56 be updated by the step just described. During the next interval of the cycle, transmitting pulses provided by the pulse generator 64 are applied to the probe 20 via switch 62, position II''. The acoustic energy transmitted toward defect 18 is reflected toward the rear wall 22 and is reflected once again from the rear wall 22, at location 24, to the receiving probe 38. The receiving probe 38 converts the reflected echo signal into an electrical signal which is attenuated in control module 56 depending upon the circuit condition of the module as determined above. The electrical signal subsequently reaches an indicator or an evaluating instrument 68 via switch 58, position II, and the amplifier 70.

The sensitivity (gain) of the amplifiers 70, 72, and 74 is individually adjustable because the transit time (path length) of the defect responsive echoes in the staggered zones in the workpiece is different. Therefore, defects of the same size in different zones in the workpiece will cause signals of different amplitudes due to the attenuation properties of the workpiece. To maintain defect signals of constant amplitude for similarly sized defects in different zones of the workpiece the gain of the amplifiers must be adjusted.

Figure 7:
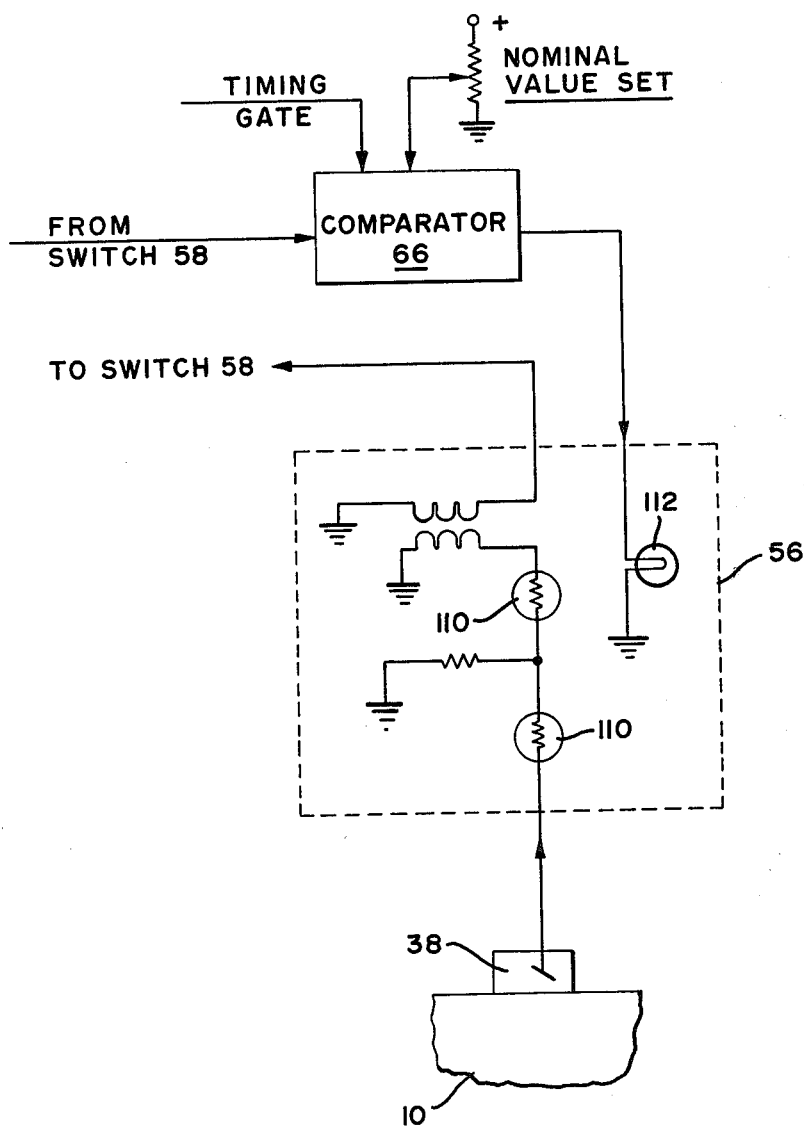
FIG. 7 is a schematic circuit diagram of a control module used in connection with the embodiment per FIG. 4.

The control module 56, see FIG. 7, typically includes a pair of series coupled photosensitive resistors 110 in series with the ultrasonic transducer. The photosensitive resistors 110 are disposed to be illuminated by an incandescent lamp 112 the brightness of which is controlled by the control signal from the nominal to actual value comparator 66. If the control signal to the lamp increases (large difference between nominal signal and reflected signal, such as is the case when the signal transmitted from the transducer probe 54 is subjected to high attenuation) the brightness of the lamp 112 increases and consequently the resistance of the photosensitive resistors 110 decreases. A decrease of the resistance of the resistors 110 provides a lower circuit impedance or greater sensitivity for the received signals. If the received signal is larger than the amplitude of the set nominal signal, the control signal reduces the brightness of the lamp 112 to a predetermined value.

In the next cycle of operation switch positions III and III'' are utilized to send a search pulse from transducer probe 28 for exploring the workpiece zone 14. If no defect is present, no signal will be received at probe 38. A defect 32 causes a reflection of the search beam toward location 24 and subsequent receipt of the ultrasonic energy by the receiver probe 38. The signal is transmitted via control module 56, switch 58, position III, amplifier 72 to the indicating circuit 68. The just described sequence is repeated when the switches 58 and 62 are set to positions IV and IV'' in the time interval for energizing the search probe 36 and associated circuits.

The nominal to actual value comparator 66 also has a timing gate input, not shown in FIG. 4. The timing gate is provided to ensure that only echoes received during a predetermined time interval (selected to correspond with the anticipated receipt of the echo signal) are processed. In this manner no random or spurious signal will be processed to change the output signal of the comparator and hence the impedance of the associated control module.

If switching is performed by electronic means as in the preferred embodiment, the sequence of probe operation occurs so rapidly that even when the probe array is mechanically moved with respect to the workpiece 10 there is practically no change in the position of the reflection location 24 during one complete cycle of operation encompassing all of the probes.

It will be understood, of course, that the pulse repetition frequency of the signal from the pulse generator 64 and applied to the probes is much greater than the frequency of switch operation so that while the switches are set for applying a search pulse to a respective probe, such as probe 20, the probe will transmit sequentially a plurality of search pulses into the workpiece before the next search probe is switched into the circuit.

Figure 6:
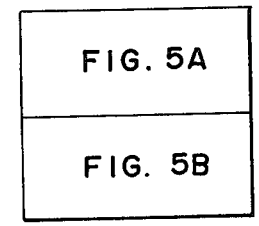
FIG. 6 shows the interconnection of the two portions of the schematic block diagram (FIGS. 5A and 5B) comprising the preferred embodiment of the invention.
Figure 5A:
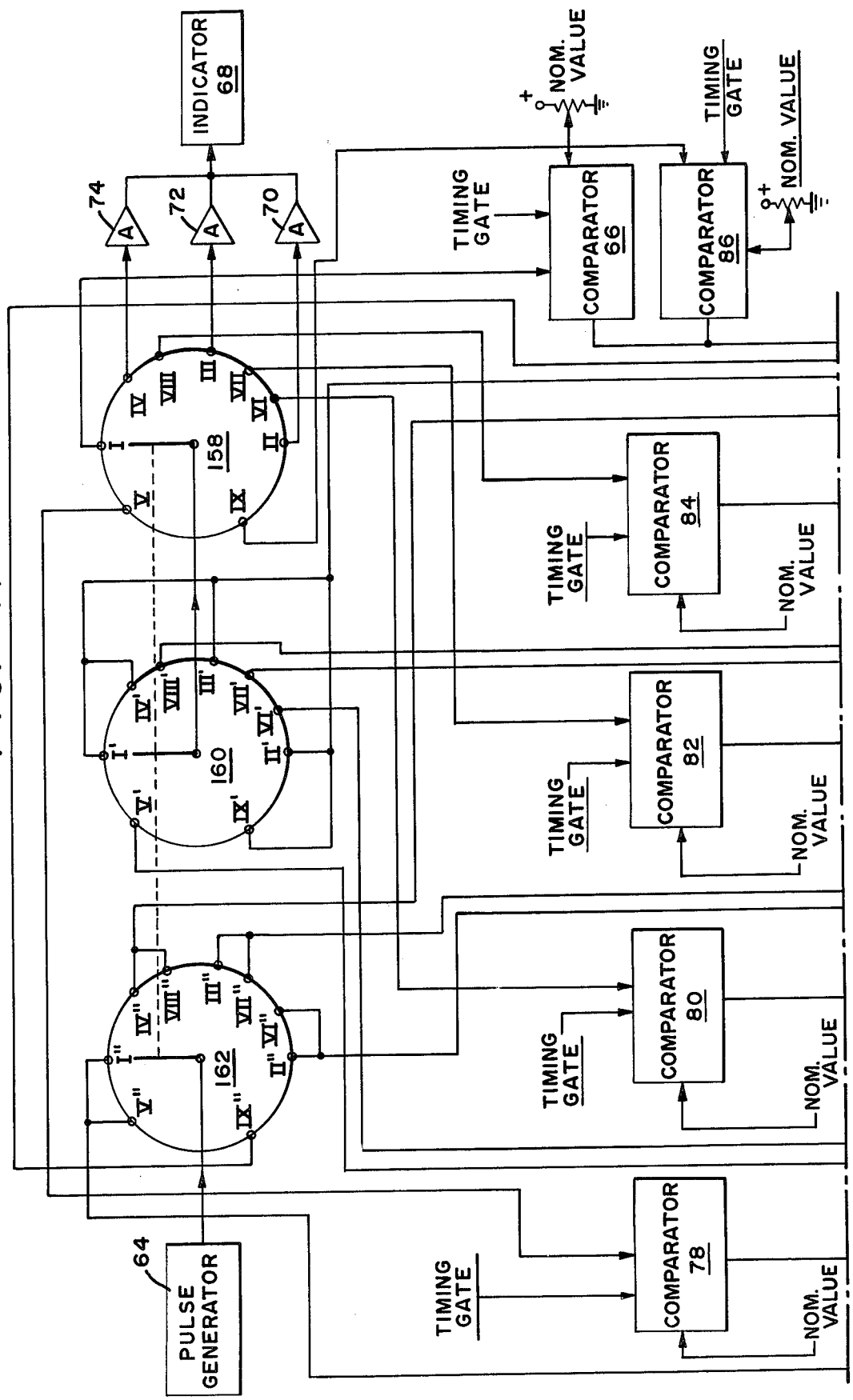
FIG. 5A is a portion of the schematic block diagram illustrating sound attenuation compensation and coupling quality compensation features of the invention and the use of the staggered test zones.
Figure 5B:
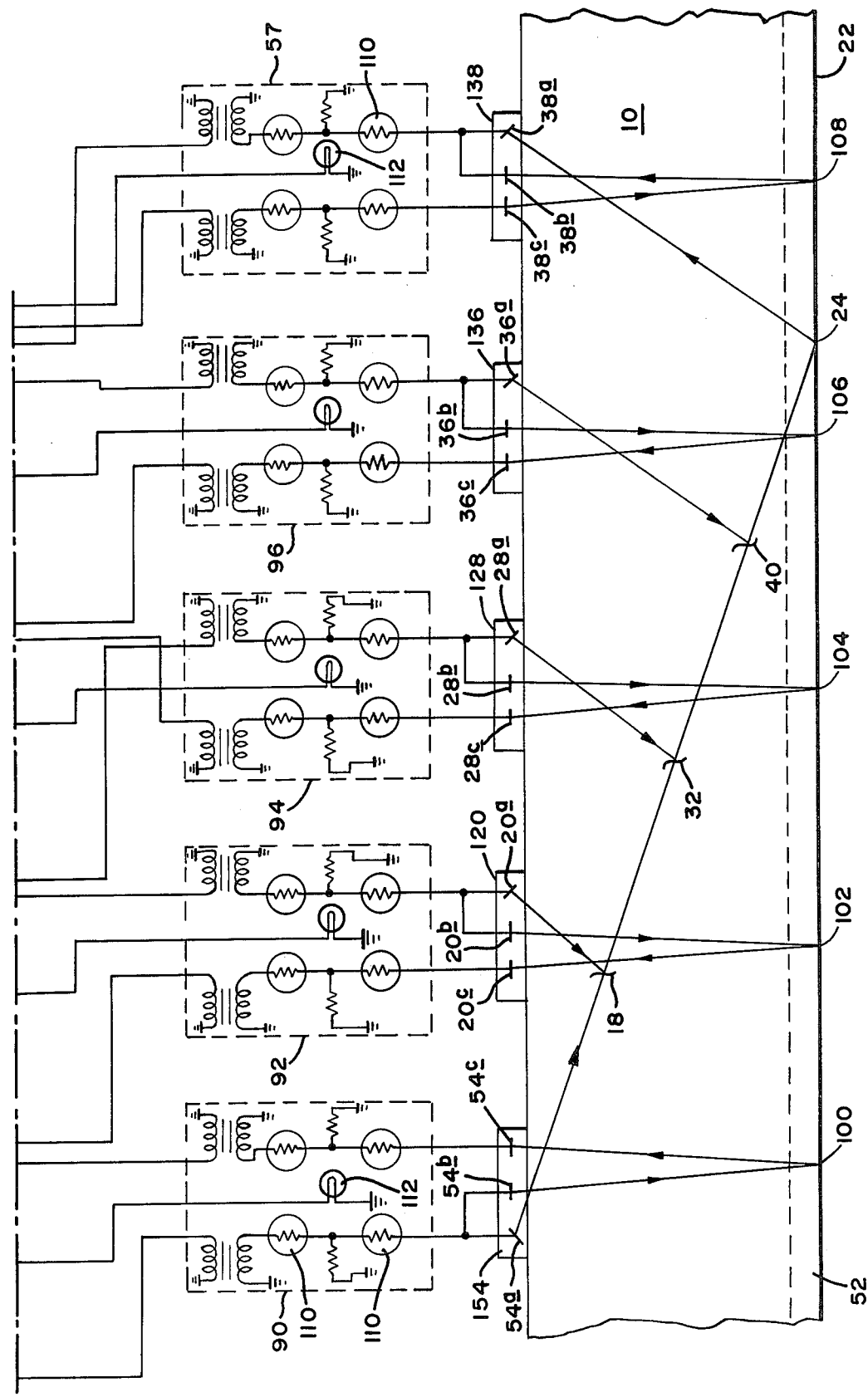
FIG. 5B is another portion of the schematic block diagram illustrating sound attenuation compensation and coupling quality compensation features of the invention and the use of the staggered test zones.

In the embodiment per FIGS. 5A and 5B, assembled as shown in FIG. 6, in addition to maintaining the echo signal amplitude signal normalized (constant for defects of equal size and orientation) by the use of a common reflection location 24, an acoustic transducer probe coupling quality compensation is provided. The acoustic coupling quality compensation is added into the cycle of operation. The purpose of the coupling quality compensation is to maintain defect responsive echo signal indication independent of the quality of acoustic coupling between the workpiece surface and the respective transducer probes involved in the test cycle. To this end, the search beam energy and the electrical signal path in circuit with the defect responsive echo signal are controlled to provide compensation for variations of the degree of acoustic coupling between the transmitter transducer probe and workpiece, and the receiver transducer probe and workpiece respectively.

The quality of acoustic coupling between a respective transducer probe and the workpiece is established by transmitting an ultrasonic search signal into the workpiece in a direction substantially normal to the entrant surface. This search signal is reflected at the rear surface of the workpiece and is received again by the same transducer probe. The amplitude of the received signal is a measure of the quality or degree of acoustic coupling between the probe and workpiece surface. It is apparent that the received signal will be weak if the quality of acoustic coupling between the respective probe and workpiece is poor. Conversely, the strength of the received signal will increase as the quality of coupling between the probe and workpiece is improved, assuming that all other variables remain constant.

The transducer probes 154, 120, 128, 136 and 138 of FIG. 5B are similar to the respective probes 54, 20, 28, 36 and 38 of FIG. 4 except that the probes have been provided with two additional transducer elements, for instance elements 54b and 54c of probe 154, to determine the quality of acoustic coupling between the respective probe and the workpiece 10. Similarly, probe 120 is provided with elements 20b and 20c; probe 128 with elements 28b and 28c; probe 136 with elements 36b and 36c; and probe 138 with elements 38b and 38c, all for the purpose of determining the quality of acoustic coupling between the respective probe and the workpiece 10.

The determination of the quality of acoustic coupling serves for controlling the energy applied to the transducer elements 54a, 20a, 28a and 36a which transmit the respective defect search ultrasonic signals. The respective energy level is controlled in relation to the degree of acoustic coupling between the associated probe and workpiece. In this manner a normalized search signal is obtained. Similarly, the described test serves also for adjusting the impedance in circuit with the element 38a, probe 138, for the degree of acoustic coupling between the probe 138 and workpiece so that the received signals are normalized for coupling quality differences.

The comparators 66, 78, 80, 82, 84 and 86 operate as has been described previously.

Switches 158, 160 and 162, FIG. 5A, have switch positions V, V', V''; VI, VI', VI''; VII, VII', VII''; VIII, VIII', VIII''; and IX, IX', IX'' for the purpose of cycling the coupling quality control test. In these positions coupling quality determination is performed for a particular probe as will be set forth in detail later.

Moreover, as compared with the embodiment shown in FIGS. 4 and 7, the control modules 57, 90, 92, 94 and 96 are modified to include two sets of serially coupled photosensitive resistors 110 which are responsive to the light output provided by the respective incandescent lamp 112 of the respective module. Typically, in module 57 one set of series connected resistors is coupled in circuit with the coupling control transmitter transducer element 38c, whereas the other set of resistors is coupled in circuit with the path traversed by the coupling control echo signal, element 38b, and the path of the signal reflected at the location 24, element 38a. The control modules 90, 92, 94 and 96 are connected similarly to the transducer elements of the respective probes.

If the switches 158, 160 and 162 are set to respective positions I, I' and I'' as shown, the pulse generator 64 via switch 162, position I'', control module 90, left hand side resistors 110, energizes the element 54a of probe 154. The element 54a, consequently, transmits an ultrasonic signal into the workpiece 10 toward location 24. The signal is reflected and is sensed, in turn, by element 38a of probe 138. The signal is converted to an electrical signal which is transmitted via module 57, right hand side resistors 110, to switch 160, position I', to switch 158, position I, to comparator 66 which generates a control signal whose amplitude is dependent upon the received signal compared with a nominal value signal supplied to the comparator circuit 66. The control signal from the comparator circuit 66 is applied to the lamp 112 of the control module 57. The module 57 is normalized for the attenuation characteristics of the location 24, but not for the coupling quality between the probe 138 and the workpiece. As recited in connection with FIG. 7, the control signal supplied to the lamp increases as the echo responsive signal from switch 158 decreases for causing the resistance provided by the resistors to decrease.

In the next sequence the switches 162, 160 and 158 are set to positions V'', V' and V. The pulse generator 64 is connected via switch 162, position V'', control module 90 to the transducer element 54a and element 54b, the latter being used for determining the quality of coupling between the probe 154 and the workpiece 10. Since the comparator 78 is responsive to the signal received by the element 54c and not to a signal received by the element 38a by virtue of the present switch setting, the signal concurrently transmitted by element 54a and reaching the element 38a is not taken into account during the period in which the impedance of the module 90 is adjusted responsive to the quality of coupling between the probe 154 and workpiece 10.

As indicated above, the pulse generator 64 via switch 162, position V'', module 90 (left hand side resistors) energizes the element 54b which transmits a sonic signal substantially normal to the workpiece entrant surface into workpiece 10. This signal is reflected at location 100 and reaches the element 54c, is conducted via module 90 (right hand side resistors), switch 160, position V', to switch 158 and from switch 158, position V, to comparator 78 which, in turn, provides a control signal to the lamp 112 in module 90. If the control signal is large, denoting a weak reflection signal at transducer element 54c resulting from low coupling quality (coupling losses) the lamp's light output is increased, thereby decreasing the resistance of the photosensitive resistors 110 and, hence, increasing the energy reaching the transmitter element 54a. This step compensates the search pulse energy applied to the transmitter element 54a for coupling losses between the probe 154 and the workpiece surface.

During the next sequential step, switches 162, 160 and 158 are set to positions IX'', IX' and IX respectively. Pulse generator 64 now is connected via switch 162, module 57 (left hand side resistors) to element 38c for determining the quality of coupling between the probe 138 and the workpiece. The transmitted signal from element 38c, reflected at location 108, is received at element 38b. The resulting electrical signal is conducted via module 57 (right hand side resistors), switch 160, position IX', switch 158, position IX, to the comparator 86. The output from the comparator 86 is fed to the lamp 112 of the module 57. The module 57 is now normalized with respect to the attenuation characteristics of the reflection location 24 as well as the quality of coupling between the probe 138 and the workpiece surface.

In the ensuing step the switches 162, 160 and 158 are set to positions II'', II' and II respectively. Pulse generator 64 now energizes the element 20a for causing a search signal. Assuming the presence of a defect 18, a defect responsive search signal after reflection at location 24 reaches the element 38a and from there is transmitted via normalized module 57 position II', switch 160, to switch 158, amplifier 70 and to indicating instrumentality 68 for indicating the defect.

In the next step the switches 162, 160 and 158 are set to positions VI'', VI' and VI respectively. Pulse generator 64 now energizes the element 20b. The reflected signal at element 20c is fed via module 92 to switches 160 and 158, positions VI' and VI respectively, to comparator 80 which provides a control signal to the lamp associated with the module 92. The module 92 is now normalized for the coupling quality between the probe 120 and the workpiece.

The steps for the remaining switch settings follow the same pattern.

It will be noted that by normalizing the modules, the impedance of the control modules 90, 92, 94, 96 and 57 is controlled in a manner to provide that the transmitting elements 54a, 20a, 28a and 36a receive a proportionately larger signal when the quality of coupling between the respective probe and workpiece is of low quality. Hence, the search signal energy is normalized and compensated for the coupling quality prevailing at a particular location. Similarly, the signal conducted by the receiving probe 138 to the defect evaluation circuit is normalized for the quality of coupling in addition for the attenuation characteristics present at the location 24 of the workpiece rear wall.

It will be apparent moreover, that one complete cycle of operation is required to obtain normalization of all circuit components. The amplitude of the rear wall echoes, for example, the signal received by element 54c resulting from the reflection location 100 will be substantially unchanged by variations in the thickness of the austenitic cladding 52 in as much as only longitudinal sound pressure waves are transmitted and received. When using transducer elements which provide a large sound-beam divergence angle, irregularities at the rear surface of the workpiece have no appreciable effect upon the amplitude of the rear wall echoes. Hence, only the integrated value of surface irregularities will be sensed and differences in the amplitude of the rear wall responsive echo signal are solely a function of the quality of acoustic coupling between the probe and the entrant surface of the workpiece.

In accordance with the invention the quantity of probes can be reduced since the transducer probe (receiving probe) associated with the probe pairs always remains the same for any combination of scanning zones. The quantity of probes $z$, compared with the known arrangements, will be reduced by the factor $z/2+1$. It is further advantageous that in any combination of scanning regions and probes a single reflection location 24 at the rear surface of the workpiece be used for reflecting the defect responsive signal. This location will shift, of course, when there is relative motion between the workpiece and the transducer probe array. The shift will be negligible during each complete cycle of the switches, encompassing operation of all probes, when high speed electronic switching means are employed.

What is claimed is:

1. An apparatus for testing thick-walled specimens by the ultrasonic pulse-echo method comprising:

at least a pair of directional transmitting probes and a directional receiving probe adapted respectively to transmit and receive ultrasonic signals along their directional axes;

said transmitting probes arranged in spaced aligned relation along one surface of a specimen and oriented thereon to direct ultrasonic signals transmitted by each probe along oblique substantially parallel paths toward a different one of a corresponding plurality of depth zones arranged in staggered relation to each other across the thickness of the specimen with the respective centers of said zones disposed along a common line defining the path of ultrasonic signals reflected in response to defects in said depth zones disposed substantially perpendicular to said one surface of the specimen;

said common line intersecting the opposite surface of the specimen at a first given location thereon at which such defect responsive ultrasonic signals are reflected across the thickness of said specimen to said one surface thereof along a common path that intersects said one surface at a second given location in spaced alignment with said transmitting probes at the side thereof remote from the initial paths of said transmitted ultrasonic signals, said receiving probe being disposed at said second given location on said one surface of the specimen with its directional axis oriented to receive said ultrasonic signals reflected along said common path from said first given location at the opposite surface of the specimen; and electrical circuit means coupled to said receiving probe for sensing the reception by said receiving probe of said defect responsive signals reflected from said first given location along said common path from any of said transmitting probes that is transmitting and for producing electrical signals representative thereof.

2. The apparatus of claim 1, in which said electrical circuit means comprise control means coupled in circuit with said receiving probe for causing adjustable attenuation of the reflected signal responsive electrical signals provided by said receiving probe, means coupled to said control means for adjusting the attenuation characteristics of said control means so that the electrical signals provided by said receiving probe and arising from defects of equal magnitude exhibit substantially the same amplitude independent of the attenuation characteristics of said first given location.

3. The apparatus of claim 1, in which said electrical circuit means comprise:

means for energizing said transmitting probes sequentially during different predetermined time intervals, indicator means having a plurality of separate input channels thereto, each of said channels corresponding to a different one of said transmitter probes, and means for applying said electrical signals selectively at any time to that one of said channels corresponding to the transmitter probe from which defect-reflected signals are expected to be received at said time.

4. An arrangement for testing thick-walled specimens as set forth in claim 1, and each probe adapted to operate during a part of the test cycle as transmitter and receiver of ultrasonic energy for sending ultrasonic energy into the workpiece and receiving reflected energy therefrom for determining the respective coupling quality of the probe with the specimen surface, and additional circuit means coupled in circuit with said respective probes for causing the respectively transmitted and received signals when processed to be compensated for differences in the coupling quality of the respective probes.

5. An arrangement for testing thick-walled specimens by the ultrasonic pulse-echo method comprising:

a plurality of transducer probes acoustically coupled to a specimen and including at least a pair of transmitting probes and a receiving probe to respectively transmit and receive ultrasonic signals;

said probes disposed in an array along the surface of the specimen to cause each transmitting probe to be associated with a respective zone of depth in said specimen, and said zones being staggered relative to each other in such a manner that the centers of said zones are disposed along a common line which intersects the rear surface of the specimen at a given location and the center axis of reflected acoustic signals responsive to signals from said transmitting probes and arising from defects in said zones, which defects are disposed substantially perpendicular to the surface of the specimen, coincides with said line, such reflected signals being received at said location and reflected therefrom along a common path toward said receiving probe for being received thereby;

control means, which include photosensitive elements disposed to be responsive to the brightness of light means, coupled in circuit with said receiving probe for providing adjustable attenuation of the reflected signal responsive electrical signal provided by said receiving probe;

electrical circuit means coupled to said control means for affecting the brightness of said light means to adjust the attenuation characteristics provided by said photosensitive elements and cause the electrical signal provided by said receiving probe and arising from defects of equal magnitude to exhibit substantially the same amplitude independent of the attenuation characteristics of said location, and indicating means coupled to said control means for indicating the presence of a defect in the specimen.

6. An arrangement for testing thick-walled specimens as set forth in claim 5 wherein the electrical circuit means comprises a comparator circuit to provide a control signal to said light means, the amplitude of said control signal being caused to decrease as the signal from said receiving probe increases over a predetermined level.

7. An arrangement for testing thick-walled specimens as set forth in claim 6, and the amplitude of said control signal being caused to assume the value of said predetermined level if the signal from said receiving probe falls below said predetermined level.

8. An arrangement for testing thick-walled specimens as set forth in claim 7, and means for energizing said transmitting probes sequentially.

9. An arrangement for testing thick-walled specimens as set forth in claim 5, and including an additional transmitting probe disposed for transmitting an ultrasonic energy signal along said common line for being received by said receiving probe after reflection at said location, said received signal, indicative of the attenuation characteristics at said location, being provided to said control means for affecting the brightness of said light means.

10. The apparatus of claim 1, comprising means responsive to said electrical signals for producing indications of said reflected defect responsive signals from any of said transmitting probes.

* * * * *